United States Patent [19]

Arndt

[11] Patent Number: Plant 6,235

[45] Date of Patent: Jul. 26, 1988

[54] **VARIETY OF *ANTHURIUM SCHERZERIANUM* NAMED ARABELLA**

[76] Inventor: Gunter Arndt, Burlo No. 29, 4280 Borken/Westf., Fed. Rep. of Germany

[21] Appl. No.: 853,352

[22] Filed: Apr. 17, 1986

[51] Int. Cl.[4] ..... A01L 5/00

[52] U.S. Cl. ..... Plt./88

[58] Field of Search ..... Plt./88

*Primary Examiner*—Robert E. Bagwill

*Attorney, Agent, or Firm*—Webb, Burden, Robinson & Webb

[57] ABSTRACT

A new and distinct variety of *Anthurium scherzerianum* is characterized by a large, round and smooth spathe of a dark orange-red stable color, a strong and compact growth, early blossoms, fast growing and resistance to common root diseases and low propagating temperatures.

1 Drawing Sheet

BACKGROUND OF THE NEW PLANT

The present invention comprises a new and distinct variety of *Anthurium scherzerianum* known by the varietal name Arabella.

The new variety is a selection from a breeding program initiated in West Germany in June of 1970.

The new variety is characterized by a large, round and smooth spathe of a dark orange-red stable color and strong flower stems. The new variety exhibits strong and compact growth and early blossoms. The new variety is resistant to common root diseases.

The propagating temperature of the new variety should not exceed 16° to 18° C. The new variety blossoms early. This early blossoming comprises an eight month period as compared to 12 to 15 months for common varieties. This blossoming can occur on miniature plants. The new variety also results in fast breeding up to medium sized to large plants.

DESCRIPTION OF THE DRAWING

The accompanying drawing illustrates the new cultivar, the color being as nearly true as possible with color illustrations of this type.

BREEDING HISTORY OF "ARABELLA"

A selection of the first generation of *Anthurium scherzerianum* parent plants from a male parent plant and a female parent plant was performed in June 1970 from A 70. The following schedule summarizes the subsequent selection activities.

(I)

September 1970: Fructification.
June 1971: Sowing.
December 1972: Blossom (selection of new male and female parent plant).

(II)

March 1973: Fructification.
November 1973: Sowing.
May 1975: Blossom (selection of new male and female parent plant).

(III)

December 1976: Fructification.
September 1977: Sowing.
March 1979: Blossom.

June 1979: Selection of female parent plant 70-AP-6-Arabella.
July 1979: Beginning of propagation by meristem (parts of the tissue of the leaf are propagated).
May 1981: Culture and beginning of first test.
June 1982: Termination of first test and destruction of the whole stock except for some female parent plants.
October 1982: Start of a new propagation by meristem for a second test.
November 1984: Beginning of cultivation for test No. 2.

COMPARISON WITH OTHER ANTHURIUM VARIETIES

Common variety: Arabella.

Amazone: More oval, smooth spathe, color a little darker, more vigorous growth, darker leaved, lower temperature degree for propagating (16°-18° C. instead of 20° to 22° C.) blossom after 8 months instead of 15 to 18 months.

Arndt's Flamenco: More vigorous growth, earlier blossom (8 months instead of 15 months) lower temperature degree for propagating (16° to 18° C. instead of 18° to 20° C.).

Renata: Larger, more oval leaves, strong growing capacity, orange-red color, more solid and larger spathe and flower stems (earlier flower (8 months instead of 12 to 15 months) lower propagating temperature (16° to 18° C. instead of 18° to 20° C.)).

DESCRIPTION OF THE PLANT

Plant:
- *Shape.*—Compact growth.
- *Leaves.*—Oval shaped, dark green, large, symmetrical.
- *Stalks.*—Solid and firm.

Spathe:
- *Texture.*—Smooth.
- *Size.*—Large.
- *Color.*—Dark orange-red.

I claim:

1. A new and distinct variety of *Anthurium scherzerianum* substantially as herein shown and described and characterized by a large, round and smooth spathe of a dark orange-red stable color, a strong and compact growth, early blossoms, fast growing and resistance to common root diseases and low propagating temperatures.

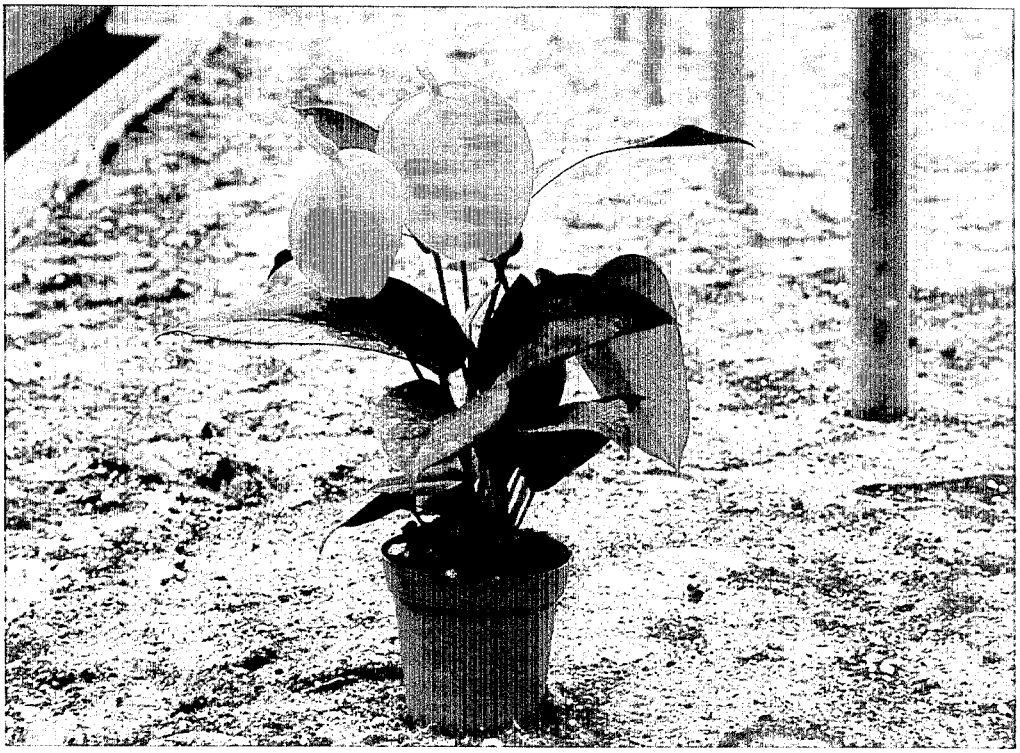

* * * * *